United States Patent
Horak (10) Patent No.: US 8,527,214 B2
(45) Date of Patent: Sep. 3, 2013

(54) SYSTEM AND METHOD FOR MONITORING MECHANICAL SEALS

(76) Inventor: Michael N. Horak, Washington, DC (US)

( * ) Notice: Subject to any disclaimer, the term of this patent is extended or adjusted under 35 U.S.C. 154(b) by 617 days.

(21) Appl. No.: 12/588,640

(22) Filed: Oct. 22, 2009

(65) Prior Publication Data

US 2010/0106429 A1    Apr. 29, 2010

Related U.S. Application Data

(60) Provisional application No. 61/108,535, filed on Oct. 26, 2008.

(51) Int. Cl.
*G01B 3/44*    (2006.01)

(52) U.S. Cl.
USPC .......... 702/34; 702/33; 702/35; 702/39; 702/42; 702/65; 702/67; 702/69; 702/75; 702/76; 702/81; 702/189; 73/7; 73/862.451

(58) Field of Classification Search
USPC .......... 702/34, 33, 35, 39, 42, 65, 67, 69, 702/75, 76, 81, 189; 73/818, 862.451, 865.9, 73/7
See application file for complete search history.

(56) References Cited

U.S. PATENT DOCUMENTS

| | | | |
|---|---|---|---|
| 4,424,973 A | 1/1984 | Heilala | |
| 4,497,493 A * | 2/1985 | Sall et al. | 277/306 |
| 4,691,276 A * | 9/1987 | Miller et al. | 700/47 |
| 4,748,850 A | 6/1988 | Kataoka | |
| 5,014,547 A * | 5/1991 | Holroyd | 73/105 |
| 5,041,989 A | 8/1991 | Kataoka et al. | |
| 5,540,448 A * | 7/1996 | Heinzen | 277/321 |
| 6,065,345 A | 5/2000 | Holenstein et al. | |
| 6,325,377 B1 | 12/2001 | Williammson et al. | |
| 6,360,610 B1 * | 3/2002 | Jarzynski et al. | 73/627 |
| 6,580,511 B1 | 6/2003 | Discenzo | |
| 6,595,523 B1 | 7/2003 | Heinzen | |
| 7,280,219 B1 | 10/2007 | Discenzo | |
| 7,533,563 B2 | 5/2009 | Horak | |
| 2002/0112533 A1 * | 8/2002 | Dunegan | 73/104 |
| 2005/0234565 A1 * | 10/2005 | Marks et al. | 700/61 |

OTHER PUBLICATIONS

Delsanto et al., "Ultrasonic texture and stress measurements in anisotropic polycrystalline aggregates," J. Acoust. Soc. Am (1990).*

* cited by examiner

*Primary Examiner* — Jonathan C Teixeira Moffat
*Assistant Examiner* — Hyun Park
(74) *Attorney, Agent, or Firm* — Merek, Blackmon & Voorhees, LLC (57) ABSTRACT

A mechanical seal monitoring system and method that measure the wear of seal faces of a mechanical seal where the mechanical seal seals a rotating machine portion from another portion of the machine. The system preferably uses a wear probe movable relative to a rotating seal component so that the wear probe can contact the rotating component. The wear of the seal is preferably determined by the relative movement that is required for the wear probe to contact the rotating component. Preferably, stress waves induced by the rubbing between the probe and the rotating component are detected by a stress-wave sensor, processed by a signal processor, and either displayed to the user numerically or reported to a monitoring computer. A signal intensity comparison method is preferably used to make the detection process insensitive to background noise generated by sources other than the contact of the wear probe and the rotating component.

22 Claims, 8 Drawing Sheets

SYSTEM AND METHOD FOR MONITORING MECHANICAL SEALS

RELATED PATENT APPLICATIONS

The subject patent application expressly claims priority from U.S. Provisional Patent Application Ser. No. 61/108,535 filed on Oct. 26, 2008 under 35 USC §119(e). The entire contents of U.S. Provisional Patent Application Ser. No. 61/108,535 are herein incorporated by reference.

TECHNICAL FIELD

This invention relates generally to methods and apparatus for monitoring wear of mechanical seals. In its most preferred form, the present invention provides a method and apparatus for providing an early indication of incipient failures of mechanical seals due to wear of their sealing faces.

BACKGROUND OF THE INVENTION

Mechanical seals provide sealing between rotating portions of a machine, e.g. a rotating shaft and another portion of the machine, e.g. a stationary machine housing. The sealing action takes place between a seal face and a seal seat, one of which rotates with the shaft while the other is stationary and attached to the machine housing. The seal seat is usually made of hard material, such as silicon carbide. The seal face is usually made of softer material, such as carbon. Therefore, as the seal face and the seal seat rotate with respect to each other while in contact, the seal face wears much faster than the seal seat. As the seal face wears over time, because either the seal face or the seal seat is axially movable and pressed axially by springs and/or fluid pressure, the seal face and the seal seat remain in contact.

There is, however, a limit to the seal face wear that the axial movement of the seal face or the seal seat can accommodate. In typical seals, this wear limit is usually between 0.04 inch (1 mm) to 0.2 inch (5 mm), depending on the seal size and its design details. Once this limit is exceeded, the mechanical seal can no longer provide sealing action and the sealed fluid will leak out of the machine through the failed seal. It is, therefore, desirable to know the extent of the wear of the seal face so that the mechanical seal can be repaired before it fails unexpectedly due to a worn seal face and disables the machine in which it is installed.

The rate at which a seal face wears depends on seal materials, speed of rotation, contact pressure, temperature, sealed fluid type, machine vibrations and other material-dependent and machine-dependent parameters and conditions. There are empirical methods for estimating the average wear rate of seal faces and they can be used to predict the average useful life of a seal. However, these are estimates of the average life and not accurate predictions of the life of a specific seal. Because of random effects that the empirical methods cannot account for, the actual useful life of two identical seals installed in identical machines can be very different.

As an example, several new identical mechanical seals could be installed in identical machines (e.g., pumps) and operated under identical conditions. If the estimated life of the mechanical seals was three years, and they were operated till the last one failed, the average life of the seals could be quite close to the predicted life of three years. However, industrial experience shows that the first seal failure could occur in less than one year. This unpredictability of the life of a specific seal face makes maintenance scheduling based on life prediction ineffective. If such scheduling was used in this pump example, it would have failed at preventing the unexpected failure of the seal that failed in less than one year. It could have also resulted in unnecessary replacement of all the seals after three years even if some could have lasted much longer.

Therefore, seal maintenance scheduling that is based on measuring the wear of the seal faces is preferred over scheduling based on life predictions. Unfortunately, the measurement of seal face wear is difficult. Seal faces are located inside machinery housings and are not easily accessed from outside. Additionally, production line machines usually rotate continuously for long periods of time and must be monitored while in operation, they often operate at high temperatures, and often involve corrosion and accumulated contamination that make accurate measurements difficult.

A simplistic and impractical method for monitoring seals is to insert a mechanical probe axially into the seal until it contacts a part of the seal that moves axially when the seal face wears, and measure the depth of insertion. The depth of insertion could be calibrated to indicate the wear level of the seal face. The main problem of this simplistic method is that the force required to assure that the probe is contacting the seal part that moves axially could disturb the seal face contact with the seal seat and the lubricating film between them, and could allow a fluid borne solid particle to enter the contact area between them. Even an extremely small particle that is harder than the seal face material would cause failure of the seal in a very short time compared to its expected life. An additional problem of this method is that it would have to be accurate to within about 0.02 inch (0.5 mm) which is difficult to achieve in the hostile environments where many seals are used.

Several methods for monitoring mechanical seals have been patented. Most of them fall into one of two categories. The first category includes methods that measure and analyze signals and physical quantities that are directly related to the state of the contact area between the seal face and the seal seat. U.S. Pat. No. 4,748,850 and U.S. Pat. No. 5,041,989 disclose methods that measure and analyze the acoustic emission generated by the sliding surfaces of the seal. Seal condition is determined by comparing the minimum, maximum and mean values of the signal to values that correspond to normal operation. The method of U.S. Pat. No. 6,065,345 also monitors and analyzes the acoustic emission from the sliding surfaces. Additionally, this method also measures the operating parameters of the monitored machine, such as temperature, pressure, power and flow rate, and adjusts the acoustic emission signal thresholds according to the operating condition.

U.S. Pat. No. 6,360,610 discloses a method that detects the collapse of the lubricating film between the seal faces of a mechanical seal. An ultrasonic transducer is placed behind one of the seal faces and used to produce ultrasonic shear waves which propagate toward the interface between the two seal faces. By monitoring the amplitudes of the waves transmitted through or reflected by the interface, the method detects film collapse and the degree of contact between the seal faces. U.S. Pat. No. 6,325,377 discloses a mechanical seal with a monitoring port in its housing and a detector assembly connected to the port. The detector assembly includes acceleration, temperature and pressure sensors, and a communication device. Condition of the seal is determined by analyzing sensor signals that the communication device transmits to a monitoring system.

None of the methods in this category have proven commercially feasible because of variety of problems. First, these methods are complex and require extensive testing before alarm threshold levels can be established. Second, the measured quantities can change over time due to operating condition changes and these changes are difficult to predict. Consequently, they may be erroneously interpreted as indications of seal failures. Third, it is difficult to determine whether changes in measured quantities are due to a seal or due to other machine components. And fourth, there is a significant level of randomness in signals generated or affected by mechanical seals so that two identical seals mounted in identical machines may produce very different signals. Consequently, none of these methods is a commercially feasible solution to the problem of monitoring mechanical seals that are installed in industrial machinery.

The second category of patented methods for monitoring mechanical seals includes those that measure the movement of a seal component that moves axially to compensate for the wear of a seal face. U.S. Pat. No. 5,540,448 discloses a method where the movement of the seal component either connects or disconnects electrically two electrodes, thus indicating that the motion has reached a certain level. U.S. Pat. No. 6,595,523 extends this method and considers motion level measurement via conductivity test of either electrical, or optical, or sonic circuits. U.S. Pat. No. 4,424,973 discloses a method where the sealing face has a weakened area and when the seal face wear reaches the depth of the weakened area a minor leak develops that is detected. The seal can then be repaired before the wear reaches a level when it could cause a major leak. U.S. Pat. No. 4,497,493 discloses a method where a radially positioned optical or magnetic sensor measures the radial distance to an axially movable seal face member. The seal face member is shaped so that its axial movement results in a change of its radius at the location where the sensor is installed. The radial distance measured by the sensor is then translated to axial wear of the seal face based on the geometry of the seal face member.

U.S. Pat. No. 4,501,429 proposes to insert a fiber optic device into the mechanical seal. A seal element carrier is provided with indicia and the optic device is focused on the indicia. One can then determine visually how much the seal face moved because of face wear. It is not explained how this method would operate with fluids that are not transparent and with fluids that deposit contamination on the optic device and on the indicia. U.S. Pat. No. 7,280,219 and U.S. Pat. No. 6,580,511 disclose methods for monitoring seals using fiber-optic technology. Optical fibers embedded within the seal facilitate measurement of pressure, temperature and wear of the seal with an apparatus that uses light sources and an interferometric system.

The hostile environments in which most mechanical seals operate limits the practicality of seal face wear measurement techniques that use various electrical, magnetic, optical and sonic sensors for measuring distance. The sealed fluid is often electrically conductive, it affects magnetic fields, and it interferes with operation of optical and sonic sensors. Over time, deposits may accumulate on the sensors and change their characteristics. Magnetic, optical and sonic sensors have a finite sensing beam width and measure distance to an area that intersects the beam rather than to a point. This makes it difficult to measure accurately axial movement with a radially-positioned sensor. Another major problem is the calibration of such wear sensors. When a sensor is first installed, it can be calibrated to provide accurate measurement of the extent of wear of a seal face. However, mechanical seals wear slowly and the seal face wear may not reach a dangerous level until years later. The ability of these sensors to remain functional and remain calibrated for years while submerged in fluid and accumulating deposits is questionable. Consequently, these methods have not proven commercially feasible.

The present invention is a seal wear monitoring method and apparatus that are unaffected by the hostile environment in which seals operate. The present invention can measure accurately the wear of a seal face and it will do so even in hostile industrial environments. Additionally, the present invention does not require re-calibration during the life of the mechanical seal, it does not require electrical or optical wiring, and it does not require advanced technical skills from the user.

SUMMARY OF THE INVENTION

It is the primary object of the present invention to provide novel and improved wear monitoring for mechanical seals that will produce an indication that the wear of a seal face reached a level where the seal face should be replaced to prevent a sudden seal failure during operation of the machine in which the mechanical seal is installed.

The detection of the wear in a mechanical seal with a rotating seal face is accomplished with a movable wear probe that, if activated, can move toward the rotating seal face and contact it or a seal component associated with it. The probe is designed to contact the rotating seal component with extremely low force that will not disturb the sealing action of the seal. The contact force can be extremely low because detection of contact is based on detection of stress waves generated at the point of contact. In the development of the present invention, experiments have shown that a wear probe made of soft material and pressed against the rotating seal component with extremely low force generates measurable stress wave signals that can be used for accurate measurement of seal face wear.

The rubbing between the wear probe and the rotating seal component generates high frequency stress waves that indicate that the wear probe made contact with the rotating component. Therefore, the level of seal face wear is directly related to the distance that the probe moved to make contact with the component. Preferably, a stress-wave sensor mounted on the wear probe, or on the seal housing, or near the seal housing, measures these stress waves. Signal processing is used to translate these high frequency signals into a numerical intensity index that can be shown on a display to indicate to the user that the wear probe is contacting the rotating seal component.

The invented method differs fundamentally from methods that are based on measurement and analysis of the acoustic emission or vibrations generated in the contact area between seal faces and seal seats due to their relative rotation. The usefulness of those methods is limited by the problems described in detail in the Background of the Invention section. The present invention is based on detection of stress waves intentionally generated with a wear probe moved into contact with a rotating seal component. Stress waves generated in the contact area between seal faces and seal seats are just an interfering background noise in the present invention and are not used for monitoring of the seals.

Furthermore, to achieve immunity to the interfering stress waves generated in the contact area between the seal face and the seal seat, testing of a seal according to the present invention is accomplished by analyzing measurements taken first when the wear probe is not activated and is not contacting the rotating seal component, and then when it is activated and could be in contact with the component. If the stress wave intensity measurement is higher with the wear probe at an activated position, a user can determine with certainty that the probe is contacting the rotating seal component and the movement of the probe is indicative of the wear of the seal face. This two-step method is independent of the intensity of the interfering stress waves because it only looks for changes in the total stress-wave intensity that occur when additional stress waves are intentionally generated with the wear probe. The intensity of the interfering stress waves is irrelevant in the invented method because it only considers these changes.

The preferred method of the present invention can be used in two different ways. With a continuously-movable and calibrated wear probe, the user can measure exactly the wear of a seal. Alternatively, the wear probe can be designed to only have one or a few calibrated positions, each calibrated to contact the rotating component at a specific level of seal face wear, such as 70% and 85%, for example. The user can then answer the question of whether the seal face wear reached or exceeded 85%, for example, by moving the wear probe to the 85% position and checking whether the probe is contacting the rotating seal component.

BRIEF DESCRIPTION OF THE DRAWINGS

The following provides a brief description of the drawings depicting various preferred embodiments of the present invention.

DETAILED DESCRIPTION OF THE PREFERRED EMBODIMENT

The preferred forms of the invention will now be described with reference to the accompanying drawings. The appended claims are not limited to the preferred forms and no term and/or phrase used herein is to be given a meaning other than its ordinary meaning unless it is expressly stated otherwise.

Figure 1:
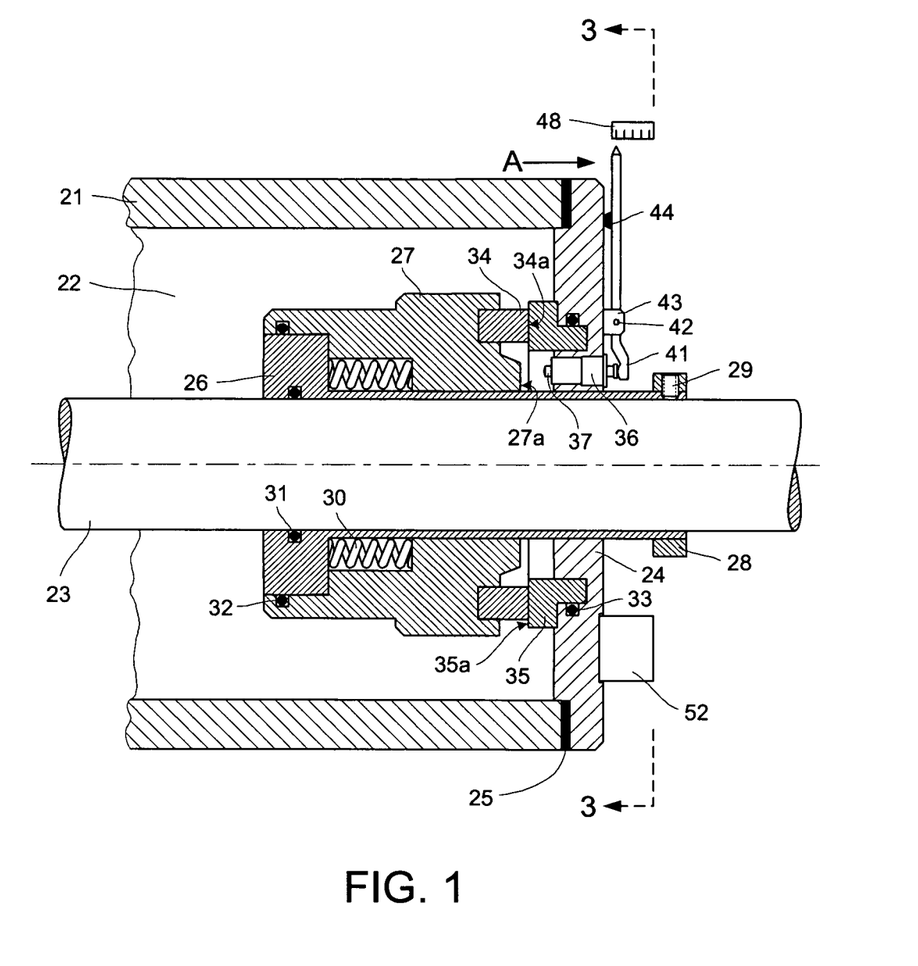
FIG. 1 is an axial section of a cartridge mechanical seal with an unactivated wear probe.

FIG. 1 illustrates a cartridge mechanical seal with rotating seal face 34 and stationary seal seat 35 for providing sealing between stationary machine housing 21 and rotating shaft 23. Cartridge mechanical seals are pre-assembled packages of seal components that make installation and maintenance simple because the entire seal cartridge is handled as a single machine part. Gasket 25 is installed between housing 21 and seal gland 24 to prevent leakage of the fluid sealed in compartment 22 through their interface. Seal seat 35 is mounted in a recess in gland 24 and gland O-ring 33 seals their interface. Cartridge sleeve 26 is attached to shaft 23 with set screws 29 that fit in threads in clamp ring 28. Shaft O-ring 31 seals cartridge sleeve 26 to shaft 23. Seal face ring 27 rotates with sleeve 26 and can slide axially on it. Seal face 34 is mounted in a recess in seal face ring 27. Springs 30 press seal face ring 27 and seal face 34 toward seal seat 35. Cartridge sleeve O-ring 32 seals springs 30 from the fluid in compartment 22. Seal face surface 34a and seal seat surface 35a are polished to high accuracy so that the fluid in compartment 22 cannot leak through their interface even when seal face 34 rotates with shaft 23 and seal seat 35 is not rotating.

As seal face 34 rotates with respect to seal seat 35, seal face 34 wears because it is made of softer material than seal seat 35. Springs 30 can compensate for small extent of axial wear of seal face 34 by sliding seal face ring 27 and seal face 34 axially along cartridge sleeve 26 toward seal seat 35. At some level of wear, a condition is reached where springs 30 can no longer provide the axial force needed for proper operation of the mechanical seal. Wear probe 36 is designed so that, when activated with activation lever 41, the wear probe sensing tip 37 will move toward sensing surface 27a of seal face ring 27 and will contact sensing surface 27a at certain level of activation. Activation lever 41 is hinged on hinge 43 and rotates around hinge pin 42. Activation lever 41 is activated by moving its other end in the direction of arrow A. Elastic bumper 44 is used to prevent vibration of activation lever 41 when it is not activated. Note that wear probe 36 is preferably installed at a location that is past the sealing surfaces of the mechanical seal and outside of the sealed compartment 22. This design keeps probe 36 clean from contamination due to the fluid in compartment 22.

One skilled in the art would realize that contacting a rotating seal component with a probe can be accomplished by numerous designs of wear probes, probe activation means and rotating seal components the probes contact. Wear probe 36 does not have to be mounted parallel to shaft 23 and does not have to move sensing tip 37 parallel to shaft 23 when activated. A wear probe can be designed that is mounted at an angle to the shaft. It is also possible to design a wear probe that is activated by rotating it and the contact with the rotating seal component can be achieved by a wear sensing surface that is eccentric with respect to the axis of rotation of the probe. Furthermore, sensing surface 27a on seal face ring 27 does not have to be perpendicular to shaft 23. In seals where the seal face to be monitored is difficult to access by a wear probe such as the one shown in FIG. 1, a wear probe can have the shape of a thin wire, allowing it to pass in between closely-spaced seal components. Additionally, the contact point between a wear probe and a rotating seal component can be inside sealed compartment 22.

Probe distance gauge 48 measures the distance that wear probe 36 moves during activation. FIG. 1 shows a schematic representation of probe distance gauge 48. In a specific embodiment, the distance can be measured and displayed by various mechanical, electrical, optical and other means. When wear probe 36 is activated with activation lever 41 and wear probe sensing tip 37 first contacts the sensing surface 27a, the reading of probe distance gauge 48 indicates the distance that wear probe 36 moved and, therefore, it measures the wear of seal face 34. Probe distance gauge 48 can be calibrated to directly display the level of wear of seal face 34.

Figure 2:
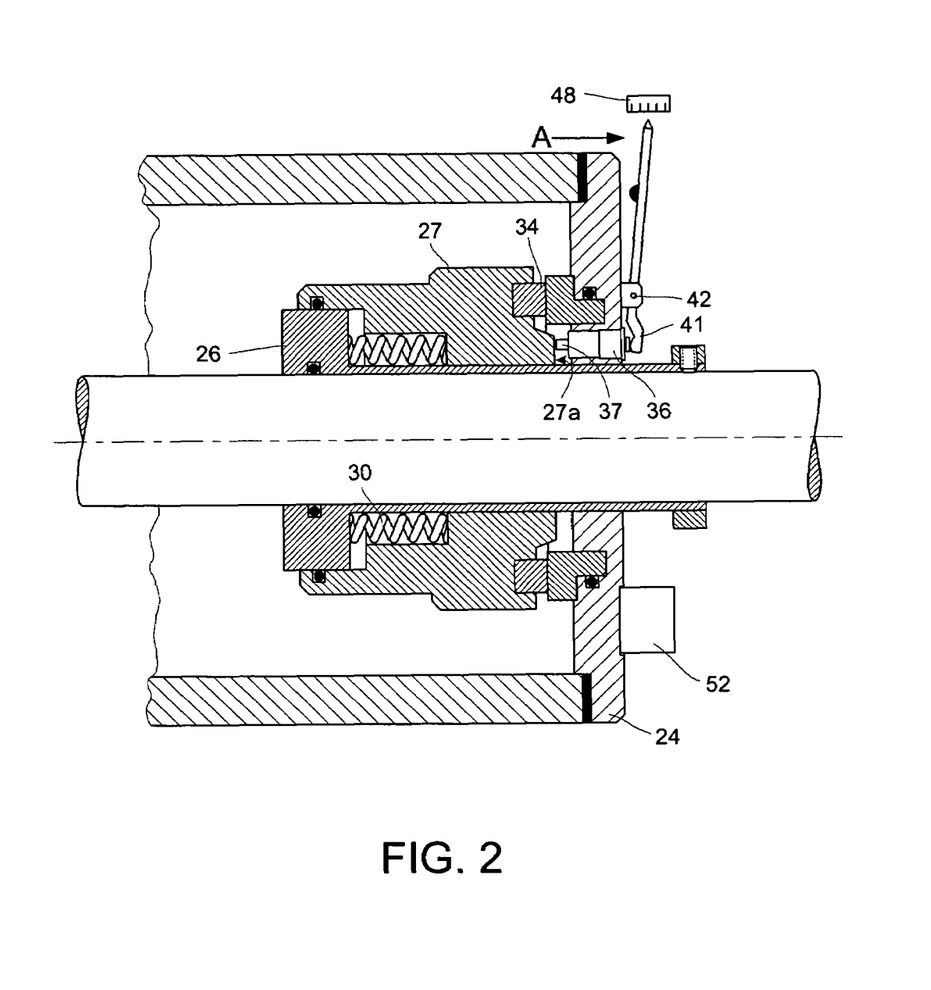
FIG. 2 is an axial section of a cartridge mechanical seal with a worn seal face and with a wear probe activated and contacting a rotating component associated with the seal face.

FIG. 2 shows the cartridge mechanical seal from FIG. 1 after its seal face 34 reached a level of wear that allowed an activated wear probe 36 to contact seal face ring sensing surface 27a. Probe distance gauge 48 now shows that the probe was moved as seen by comparing the gauge readings in FIG. 1 and FIG. 2. The reading of probe distance gauge 48 in FIG. 2 is indicative of the wear of seal face 34.

Wear probe sensing tip 37 in FIG. 2 is contacting the rotating seal face ring sensing surface 27a. This contact, between the rotating seal face ring 27 and wear probe tip 37, generates stress waves that indicate that the seal face has reached a certain level of wear. The stress waves propagate from wear probe tip 37 through wear probe 36 into gland 24.

Figure 3:
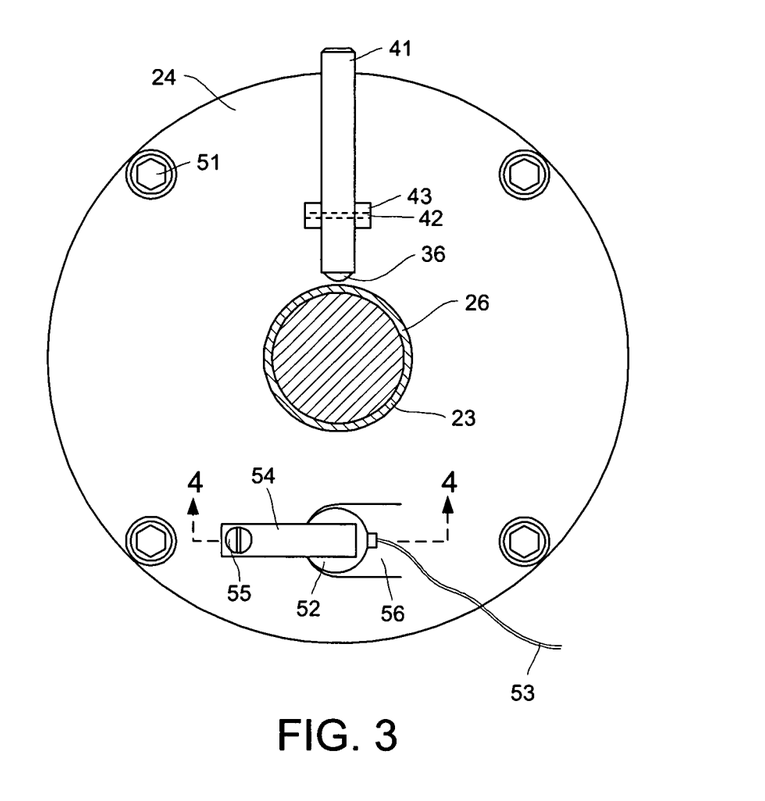
FIG. 3 is a sectional view taken along line 3-3 in FIG. 1, illustrating a seal gland with a stress-wave sensor and a wear probe activation lever mounted on it.
Figure 4:
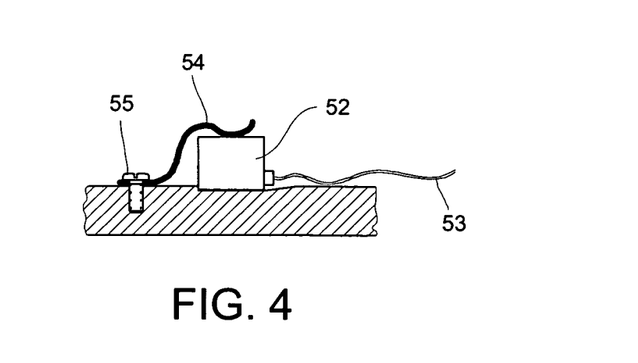
FIG. 4 is a sectional view taken along line 4-4 in FIG. 3, illustrating in detail how a sensor is attached to a seal gland.

The generated stress waves are measured by stress-wave sensor 52 that is attached to gland 24 as illustrated in FIG. 3 which is a sectional view taken along line 3-3 in FIG. 1. It shows sensor 52 attached to seal gland 24 with an elastic sensor holder 54 that is attached to gland 24 with sensor holder screw 55. Sensor seat 56 is a recessed machined surface on gland 24 that serves as a seat for sensor 52 and keeps the sensor from moving. Sensor seat 56 is machined to be straight and smooth to facilitate good transmission of stress waves from gland 24 to sensor 52. Also, sensor seat 56 is preferably located close to wear probe 36 to provide a short stress-wave propagation path from wear probe tip 37, shown in FIG. 1, to sensor 52. FIG. 3 also shows screws 51 that attach gland 24 to housing 21, shown in FIG. 1. The figure also illustrates the location of the activation lever 41 and hinge pin 42 about which activation lever 41 rotates. FIG. 4 is a sectional view taken along line 4-4 in FIG. 3. It shows the details of the attachment of sensor 52 to gland 24 with elastic sensor holder 54.

One skilled in the art would realize that sensor 52 can also be attached to machine parts or seal parts other than gland 24. It could be attached to a part of the machine in which the mechanical seal is installed, or it could be attached directly to wear probe 36.

The contact force between wear probe tip 37 and seal face ring sensing surface 27a that is required for generating measurable stress waves is very low. Experiments, in the developments of the present invention, have shown that even a force as low as 0.05 lb (0.22 Newton) is sufficient. Mechanical seals are often designed so that the pressure between seal face 34 and seal seat 35 developed by springs 30 is at least 10 psi (0.69 bar) when the seal face is worn down to its allowed limit. For typical seals with contact areas of 1 in$^2$ (6.5 cm$^2$) or larger, the contact force that is given by the product of the pressure times the force is, therefore, 10 lbs (44 Newton) or larger. The maximum force that wear probe tip 37 can apply on seal face ring 27 must be a small fraction of this spring force in order not to disturb the sealing action of the mechanical seal during the seal wear test. Therefore, it is desirable to limit the maximum contact force to a value of 5% or less of the minimal spring force, or 0.5 lb (2.2 Newton) in this case. Since the present invention can operate with a force as low as 0.05 lb (0.22 Newton), this requirement is easily met.

Experiments, in the developments of the present invention, have shown that the contact force between wear probe tip 37 and seal face ring sensing surface 27a that is required for generating measurable stress waves is very low even when seal face ring sensing surface 27a is polished. The required contact force can be reduced even further by providing a textured finish to sensing surface 27a because a textured surface generates stress waves with higher intensity.

Figure 5:
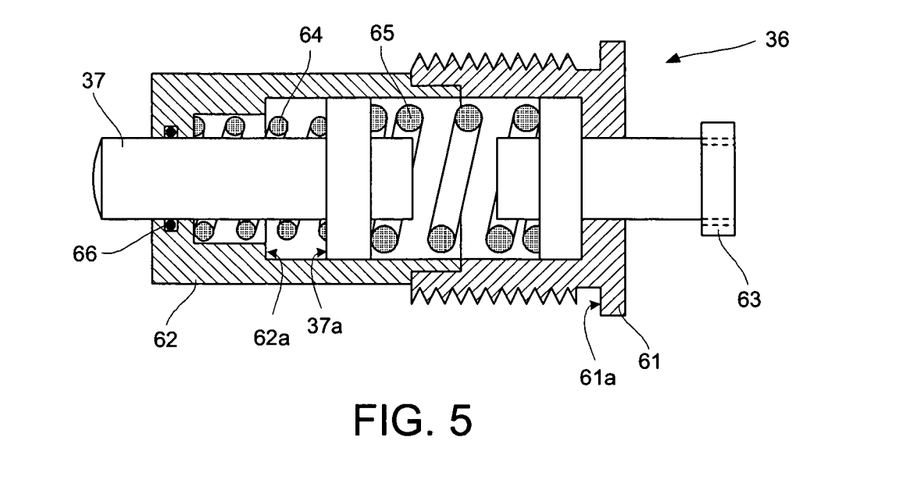
FIG. 5 is an axial section of an unactivated wear probe.

FIG. 5 is an axial section of unactivated wear probe 36 showing its force-limiting design for embodiments where wear probe 36 is designed to detect a specific level of seal face wear. Wear probe 36 is enclosed in a cylindrical body consisting of upper body 61 and lower body 62 that are firmly attached to each other. Upper body 61 is threaded and its thread fits in a threaded hole in gland 24. Upper body surface 61a is used to assure that upper body 61 is threaded all the way into gland 24 so that the axial location of wear probe 36 is precise with respect to gland 24. The activation force is applied to plunger 63. This force is transmitted through force-limiting spring 65 to probe tip 37 that is made of relatively soft material, such as teflon. Probe O-ring 66 prevents contamination from entering wear probe 36. Return spring 64 keeps probe tip 37 retracted into the lower housing 62 when wear probe 36 is not activated. Wear probe 36 is dimensioned so that when it is unactivated and probe tip 37 is retracted, it cannot contact seal face ring 27 even if seal face 34 is worn down to its allowed limit. However, it will be readily appreciated that the monitoring system of the present invention could be designed such that when the seal face is worn to a predetermined level, the seal face ring 27 contacts wear probe 36 without the wear probe 36 moving.

Figure 6:
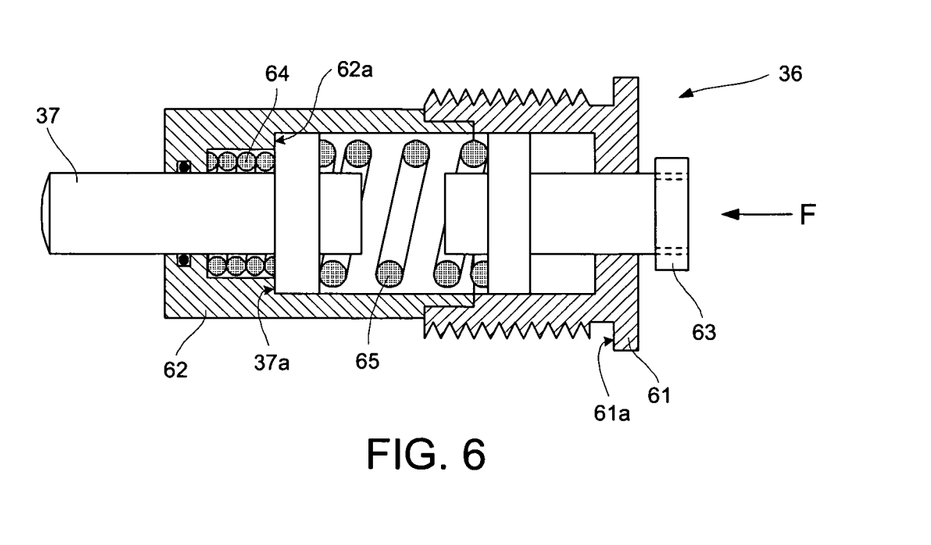
FIG. 6 is an axial section of an activated wear probe.

FIG. 6 is an axial section of wear probe 36 when it is activated by an axial force represented by the arrow F. This force is applied by the activation lever 41 as shown in FIG. 2. FIG. 6 shows that in the activated state of wear probe 36, return spring 64 is compressed and surface 37a on probe tip 37 is in contact with surface 62a on lower body 62. This contact results in a precise movement of probe tip 37 out of wear probe 36, in the direction of the activation force F. Force-limiting spring 65 is not fully compressed when probe 36 is activated. Therefore, probe tip 37 cannot transmit force that exceeds the force required to compress force-limiting spring 65. This force-limiting mechanism prevents probe 36 from applying force on a rotating seal component that exceeds a limit above which probe 36 could disturb the sealing action of the seal face and the seal seat.

One skilled in the art would realize that force limiting of the wear probe can be realized in numerous other ways. For example, the probe tip can be made of elastic material that compresses or bends due to the contact force, thus limiting the force it can transmit. Alternatively, the probe can include pneumatic, hydraulic or electrical means of limiting the contact force.

The level of seal face wear at which the activated wear probe 36 contacts seal face ring 27 is determined by the axial dimensions of gland 24, wear probe 36, seal seat 35, seal face 34, cartridge sleeve 26 and seal face ring 27. Except for the wearing seal face 34 that is being monitored, none of the other components change their axial dimensions during the life of the mechanical seal. Therefore, this seal wear measurement method never needs re-calibration.

Wear probe tip 37 is made of substantially soft material, such as teflon. Because the contact force between probe tip 37 and seal face ring 27 is limited to a very low value by force-limiting spring 65, very little surface damage can be caused to probe tip 37 during testing of a worn seal face. No damage at all will be caused to the metallic seal face ring 27 when it is contacted by the relatively soft probe tip 37. However, it is also possible to allow probe tip 37 to wear when contacting rotating seal face ring 27. In embodiments where the objective is to detect a specific wear level of seal face 34, probe tip 37 can be allowed to wear during the detection of the specific wear level of the seal face because the function of probe tip 37 ends once the wear is detected. Following the detection, the seal will be rebuilt and probe tip 37 will be replaced.

When an activated wear probe 36 contacts surface 27a in a worn seal, as shown in FIG. 2, stress waves are generated at the point of contact. These waves are microscopic deformations that travel through metal at the speed of sound in the metal. The energy of a stress wave is extremely low because it does not involve a net movement of mass. Stress waves should not be confused with mechanical vibrations that consist of rigid-body motions of machine parts or large elastic deformations of machine parts and, therefore, involve much larger energy levels associated with the moving mass of the machine parts. This fundamental difference can be appreciated if one rubs a finger gently against a large metallic machine part. The rubbing generates measurable stress waves in the machine part but it does not generate vibrations of the machine part.

Stress waves propagate in all directions away from the point of contact where they are generated. Some waves pass through wear probe 36 into gland 24 and reach sensor 52 shown in FIG. 2. Sensor 52 can be a piezoelectric stress-wave sensor that generates electrical charge in response to stress waves. In such a sensor, stress waves strain a piezoelectric crystal mounted inside a sensor housing which is attached to the machine part that is subjected to stress waves. The output of sensor 52 is connected to electronic signal processing hardware with sensor cable 53, as shown in FIG. 7.

Figure 7:
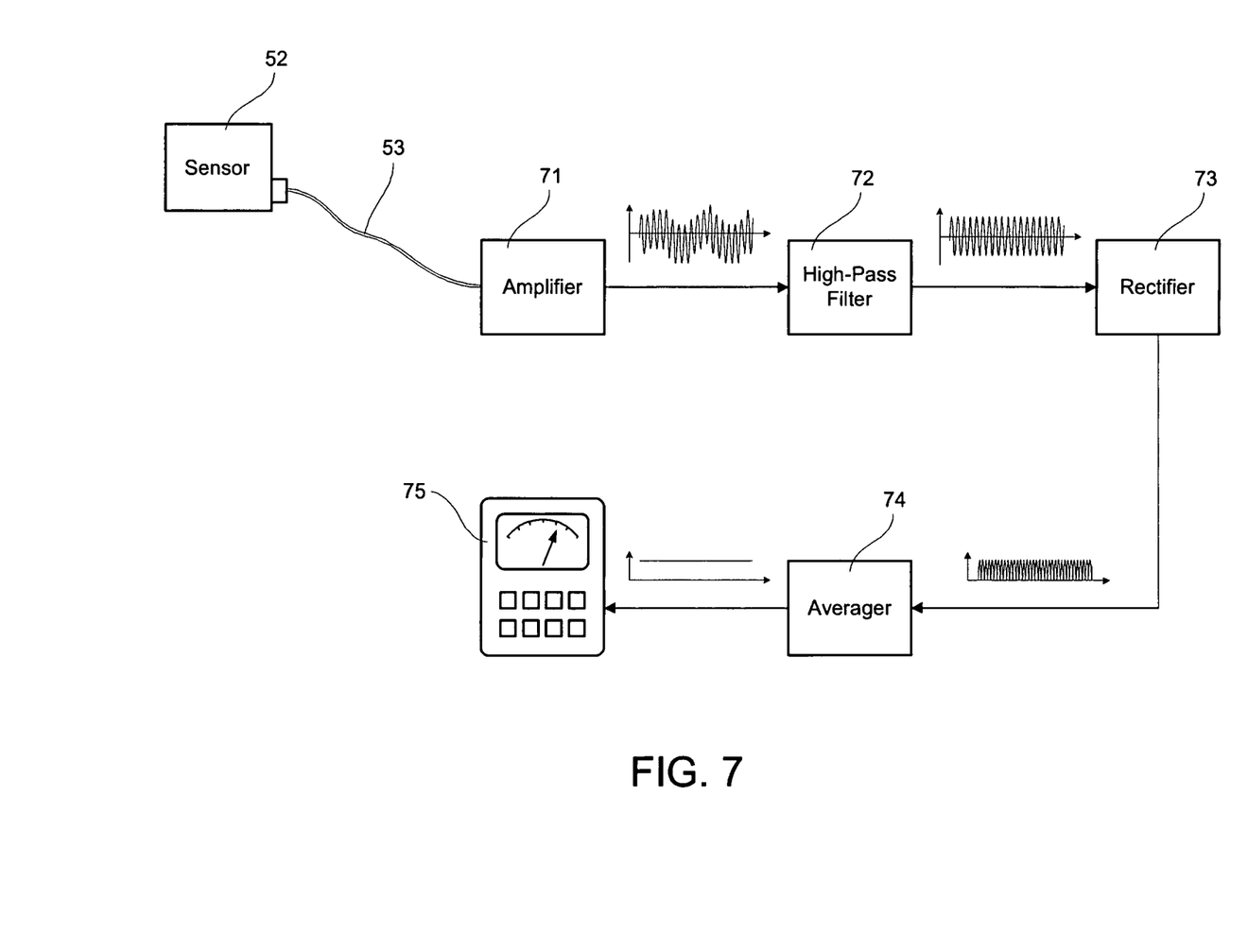
FIG. 7 is a block diagram of the signal processing that extracts a stress-wave intensity index from the output of a stress-wave sensor.

The electrical charge generated by sensor 52 is converted into an electrical signal and is amplified by amplifier 71 shown in FIG. 7. Amplifier 71 can be internal to sensor 52 or external to it. Sensor 52 may also measure interfering signals due to low-frequency sources originating in the machine in which the mechanical seal is installed. These signals are typically below 10 kHz and are interfering with the stress waves that carry the information on the wear of the seal. The waveform shown at the output of amplifier 71 illustrates the presence of the low-frequency interference in the high-frequency stress wave signal. High-pass filter 72, set at a frequency higher than the frequency of the interfering signals, is used to filter out this low-frequency interference. The waveform shown at the output of high-pass filter 72 is free of the low-frequency components. The signal is then rectified by rectifier 73 and the rectified waveform is then averaged by averager 74. The output of averager 74 is a DC signal with a magnitude that is proportional to the amplitude of the high-frequency stress wave. In the present invention, sensor 52 does not have to be a piezoelectric stress-wave sensor. A sensor based on other physical principles that can measure stress wave intensity can also be used.

The magnitude of the averaged waveform is measured by voltage meter 75. The meter can be analog, digital, or one with a graphical display of voltage versus time. When wear probe 36 is activated and meter 75 displays a voltage that is higher than the background voltage level of the machine, one can be certain that wear probe 36 contacted seal face ring 27 and generated stress waves. If the voltage remains unchanged at the background level when wear probe 36 is activated, then wear probe 36 did not contact seal face ring 27.

A key advantage of the preferred seal wear monitoring method is that it is based on detecting differences between signal levels rather than being based on precise measurements of signal levels that are then compared to a priori set thresholds. Consequently, the invented seal wear monitoring method does not require a priori knowledge of the background noise level of the machine or a priori knowledge of the expected signal level when there is, contact between the wear probe tip and a rotating seal component. Furthermore, this method does not even require a precisely calibrated stress wave sensor. A sensor that can detect a signal level difference is all that is required to determine that a seal face is worn.

Manual testing of a mechanical seal for seal face wear that reached a specific level is performed as follows. The user first attaches sensor 52 to seal gland 24 by inserting it under sensor holder 54, as shown in FIG. 3 and FIG. 4. Alternatively, the user can use any other attachment methods, such as a magnetic holder. The sensor is connected with sensor cable 53 to an instrumentation subsystem that includes the signal-processing functions illustrated by blocks 71, 72, 73 and 74 and meter 75, all shown in FIG. 7.

The user then reads the background signal level corresponding to an unactivated wear probe 36 as it is measured by meter 75. He then pushes activation lever 41 in the direction of arrow A in FIG. 1 and reads the signal level measured by meter 75 while lever 41 activates wear probe 36. If the activated signal level is at least 25% higher than the background signal level, the user declares the seal worn. If the activated level is equal to or lower than the background level, the user declares the seal unworn. If the voltage level when wear probe 36 is activated is higher but by less than 25% than when it is unactivated, the user can repeat the test several times to get more reliable diagnosis. The test sequence can consists of a 2-second activation followed by a 2-second de-activation, repeated three times. If all three measured levels during the activation periods were higher by at least 10% than the three measured levels during de-activation, one can be certain that probe 36 contacted a rotating seal component and the seal is worn. Otherwise, the seal is declared unworn and the measurement fluctuations are attributed to random fluctuations of the background noise.

For a specific seal, the user can develop customized testing procedures that best suit the specific application. Such a customized test can use different activation/de-activation periods, different number of test repetition cycles, and different signal level margins than those mentioned above.

Manual measurement of the exact wear level of a seal face of a mechanical seal is accomplished as follows. The user first attaches sensor 52 to seal gland 24 by inserting it under sensor holder 54, as shown in FIG. 3 and FIG. 4. Alternatively, the user can use any other attachment methods, such as a magnetic holder. The sensor is connected with sensor cable 53 to an instrumentation system that includes the signal-processing functions illustrated by blocks 71, 72, 73 and 74 and meter 75, all shown in FIG. 7.

The user then reads the background signal level corresponding to an unactivated probe 36 as it is measured by meter 75. He then manually advances activation lever 41 slowly in the direction of arrow A in FIG. 1 up to a distance when the signal level measured by meter 75 suddenly increases and is 25% higher than the background level. The user then determines the wear level based on the reading of probe distance gauge 48. If the activated level never increases above the background level, the user declares the seal unworn. If the activated level increases above the background level but by less than 25%, the user will perform a three-cycle activation/de-activation test that was described above to confirm that the probe is really contacting the rotating seal component when the activation level is the one displayed on probe distance gauge 48.

For a specific seal, the user can develop customized testing procedures that best suit the specific application. Such a customized test can use different activation/de-activation periods, different number of test repetition cycles, and different signal level margins than those mentioned here.

Automatic testing of a mechanical seal according to the present invention can be performed as described next. Sensor 52 is either permanently attached to gland 24 with sensor holder 54, or is permanently cemented to gland 24, or is attached with a threaded stud that is an integral part of the sensor case and fits in a threaded hole in gland 24, or is attached by any other means to the seal or to the machine. Sensor 52 is connected with sensor cable 53 to an instrumentation system that performs the signal-processing functions illustrated by blocks 71, 72, 73 and 74 shown in FIG. 7. The output of averager 74 is connected to an analog-to-digital converter input of a monitoring computer. The computer has an output that controls remotely-controlled actuator 68 shown in FIG. 8. The control signal can be electrical, either analog or digital, or fiber-optic, or any other signal type. Actuator 68 can be electromagnetic, pneumatic, hydraulic, piezoelectric, or any other type.

Figure 8:
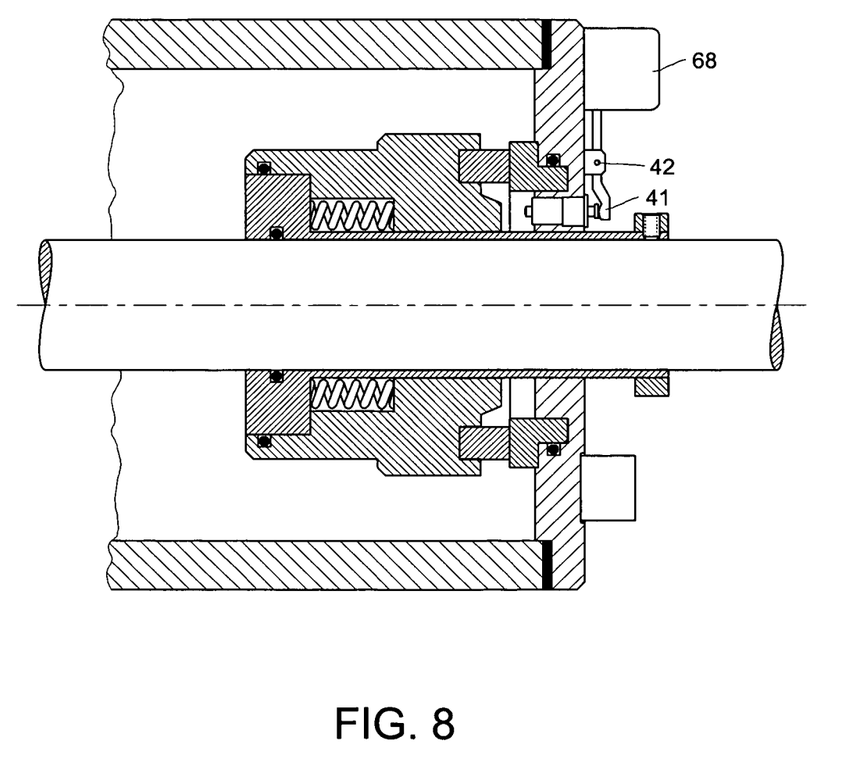
FIG. 8 is an axial section of a cartridge mechanical seal with an unactivated wear probe and an activation mechanism that uses a remotely-controlled actuator.

The automatic testing procedures are similar to the manual procedures. The computer first measures the background signal level by sampling the voltage at the output of averager 74. The computer then commands actuator 68 to activate the wear probe a distance corresponding to wear level to be detected and it measures the activated signal level at the output of averager 74. If the activated level is 25% higher than the background level, the computer declares the seal worn. If the activated level is equal or lower than the background level, it declares the seal unworn. If the activated level is higher than the background level but by less than 25%, the computer will perform a three-cycle activation/de-activation test that was described above and it will determine the state of the seal based on this test. The automated testing procedure can be performed on a regular basis, such as daily, weekly or monthly. One monitoring computer can monitor many mechanical seals.

Rather than detecting a specific wear level, the exact wear level of seal face 34 can be measured automatically, similarly to the manual process of measuring it. The computer first measures the background signal level by sampling the voltage at the output of averager 74. The computer then commands actuator 68 to slowly move wear probe tip 37 up to a distance where the signal level measured at the output of averager 74 is 25% higher than the background level.

The computer then determines the seal wear level based on that distance. If the activated signal level never increases above the background level, the computer declares the seal unworn. If the activated level is higher than the background level but by less than 25%, the computer will perform a three-cycle activation/de-activation test that was described above to confirm that the probe is really contacting the rotating seal component at the activation level that actuator 68 applies.

Since the computer can sample and store a time history of the output of averager 74, it can perform more accurate seal testing than a human user who only reads the mean value of averager 74 output. For example, the computer can compute the mean, the 10% cumulative amplitude density function value and the 90% cumulative amplitude density function value of averager 74 output and apply the signal level test, with appropriate thresholds, to all three quantities rather than testing only the mean value. The computer may decide that probe tip 37 contacted a rotating seal component only if all three quantities indicate so. This testing procedure will further increase the accuracy of the test. One skilled in the art would realize that there are many other computable indices that can be used by the computer for comparing signal levels of the output of averager 74 in addition to the cumulative amplitude density function levels.

When the present seal monitoring method is implemented automatically, the wear probe 36 force limiting method can be implemented in actuator 68 rather than by means of force limiting mechanism that is inside wear probe 36, as shown in FIG. 5 and FIG. 6. The force of an electromagnetic actuator can be limited by limiting the current to it. The force of pneumatic and hydraulic actuators can be limited by limiting their fluid pressure. When the force is limited by actuator 68, wear probe 36 no longer needs force limiting spring 65. Therefore, plunger 63 and probe tip 37 can be replaced with a single solid plunger with its end serving as the probe tip.

The background signal level measured by sensor 52 when wear probe 36 is unactivated is not known prior to the measurement. It is desirable for this level to be less than one half of the full voltage range of meter 75 or the full input range of a monitoring computer so that if the activated signal level is twice as high, it can be measured without saturating the meter. It is also desirable for the unactivated signal level to be above 5% of the full range, to assure that the background signal is being measured accurately. Consequently, it is advantageous for amplifier 71 to have variable gain so that by changing its gain the unactivated signal level can be placed between 5% and 50% of the full input range of meter 75.

The automatic gain adjustment process is as follows. Amplifier 71 has computer-controlled gains of 1, 5, 25 and 125. When measurement of the unactivated level is performed, the control computer sets the gain initially at 5 and measures the level. It then selects one of the four gains that will bring the signal level to the desired range of 5% to 50% of full range, and repeats the unactivated level measurement. Gain selection may require more than one such iteration. The activated level measurement is then performed with the selected gain in effect. This process guarantees that a signal level increase of up to a factor of two can always be measured accurately. The number of gains can be other than four and their values can be other than 1, 5, 25 and 125, as long as they achieve the goal of accurately measuring signal level changes. The range of 5% to 50% can also be different as long as it supports accurate measurements.

Calibration of wear probe 36 in the present invention is simple and it does not have to be repeated during the life of the seal face it is monitoring, even if its life is many years. Before a seal is put in service and, therefore, its seal faces are still unworn, a special calibration probe is used to measure the distance D wear probe 36 would have to move to contact the rotating seal component. In installations where the goal is to detect a specific seal face wear, such as decrease of its original thickness by W inches (or millimeters), the movement of wear probe 36 when activated is set to D−W. This assures that wear probe 36 will contact the rotating seal component if it moves distance D−W and the seal face wear is W.

In installations where the goal is to measure the wear of a seal face from its original thickness, distance D measured as specified above is used as a calibration constant. If wear probe 36 first contacts the rotating seal components in a worn seal when it is moved distance L, the wear of the seal face, expressed as decrease of its thickness, can be computed by W=D−L.

Alternate Embodiments

FIG. 1 shows a cartridge mechanical seal with a rotating seal face and a stationary seal seat. This invention is not limited to this specific seal configuration. It can be applied to mechanical seals that do not use a cartridge, seals where the seal seat rotates and the seal face is stationary, dual seals with two seal faces and two seal seats, or any other seal configuration.

Figure 9:
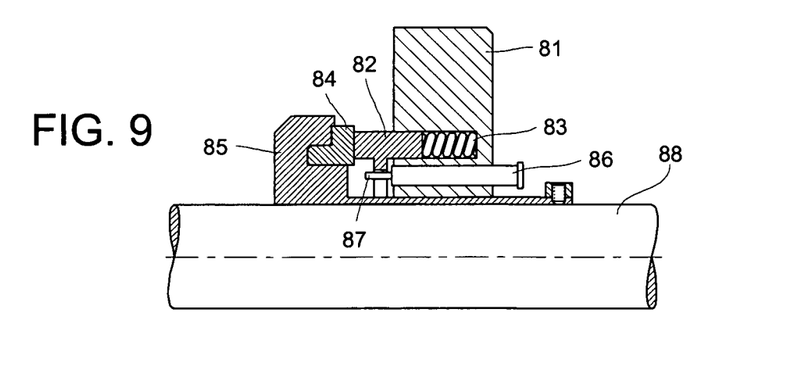
FIG. 9 is an axial section of a cartridge mechanical seal with an unworn stationary seal face and an unactivated wear probe.

FIG. 9 shows an embodiment of the present invention applied to monitoring of a mechanical seal with a rotating seal seat 84 and a stationary but axially movable seal face 82. The stress waves that indicate seal face wear are produced in this case between probe tip 87 and rotating cartridge sleeve 85 that is axially fixed. FIG. 9 only shows the main components of this embodiment and only the portion of the axial section that is above shaft 88.

Stationary seal face 82 is located in a recess in stationary seal-face gland 81 and can slide in the recess axially. Seal-face springs 83 press stationary seal face 82 toward rotating seal seat 84 which is rigidly mounted in rotating cartridge sleeve 85. Probe 86 can move axially in a hole machined through seal-face gland 81. FIG. 9 does not show the activation means for probe 86 that are similar to those described above for other seal embodiments. Probe 86 is shown unactivated in FIG. 9 and stationary seal face 82 is shown unworn.

Figure 10:
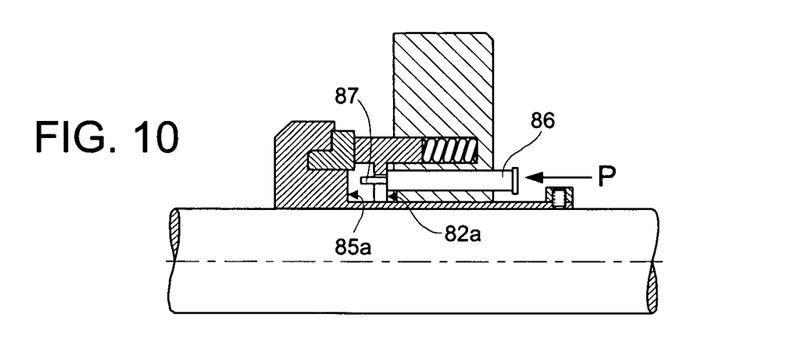
FIG. 10 is an axial section of a cartridge mechanical seal with an unworn stationary seal face and an activated wear probe.

FIG. 10 shows the seal from FIG. 9 with probe 86 activated by pushing it in the direction of the arrow P until it contacts stationary seal-face surface 82*a*. FIG. 10 shows that when probe 86 is activated, probe tip 87 does not contact rotating cartridge sleeve surface 85*a*. It is so because stationary seal face 82 is unworn.

Figure 11:
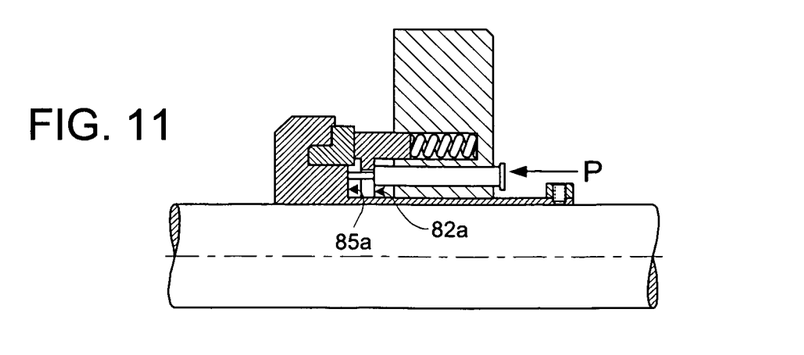
FIG. 11 is an axial section of a cartridge mechanical seal with a worn stationary seal face and an activated wear probe.

FIG. 11 shows the seal from FIG. 10 with stationary seal face 82 worn to the level where wear detection is desired. Because stationary seal face 82 is worn, stationary seal-face surface 82*a* moved axially in the direction of arrow P and so did the activated probe 86 that moves together with stationary seal-face surface 82*a*. Probe tip 87 now contacts the rotating cartridge sleeve surface 85*a* and stress waves are generated due to rubbing at their point of contact. The detection and processing of the stress waves is similar to what was described above for other seal embodiments.

FIG. 9, FIG. 10 and FIG. 11 show an embodiment for determining if a seal with stationary face and rotating seal seat reached a specific level of seal face wear. One skilled in the art would realize that this embodiment can be modified to provide a measurement of the exact level of seal face wear in a way similar to the method for measuring level of seal face wear in a seal with stationary seal seat and rotating seal face. This modified embodiment utilizes a continuously movable and calibrated probe tip 87 that moves with respect to probe 86 in a seal such as the one shown in FIG. 10. The continuously movable and calibrated probe tip 87 provides a measurement of the level of seal face wear in the seal by detecting the position of probe tip 87 that results in increased intensity of the measured stress wave signal.

In yet another embodiment, one mechanical seal of any type can be outfitted with several wear probes, each dimensioned to detect a different level of seal face wear. For example, with three wear probes set at 60%, 75% and 90% of allowed seal face wear, the user can determine if the wear of the seal face is below 60%, between 60% and 75%, between 75% and 90%, or above 90% of allowed wear. This provides more accurate monitoring of the wear of the seal face.

Furthermore, one of the wear probes can have a probe tip made of harder material than the other probes, but softer than the rotating seal component against which it is pressed. This probe can be used for removing deposits from the rotating component so that the measuring probe (or probes) does not generate incorrect measurements when it rubs against deposits on the rotating seal component.

In yet another embodiment, wear probe 36 in FIG. 1 can be a fixed one that does not require activation. Probe tip 37 can be at such a fixed location that once the wear of seal face 34 reaches the predetermined limit, seal face ring 27 will contact probe tip 37. A mechanical seal monitoring system that utilizes a fixed probe preferably has its sensor signal monitored continuously because the signal will increase only once, when the contact occurs for the first time. Once probe tip 37 and seal face ring 27 are in contact, they will wear together and the signal intensity will remain relatively constant. This is not a preferred application of this invention for the typical industrial seal-monitoring setting because if the time of the first contact is missed, the seal wear will not be detected. However, this embodiment of the present invention can be useful in special situations.

Figure 12:
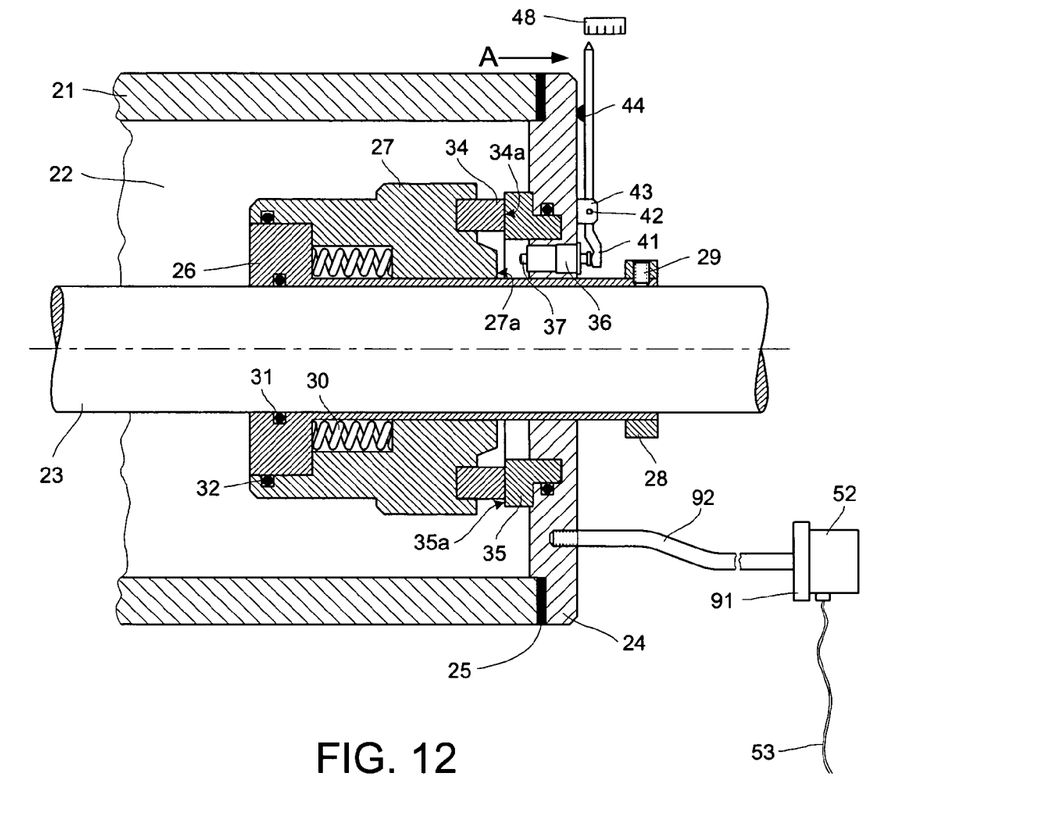
FIG. 12 is an axial section of a cartridge mechanical seal with a remotely-located stress-wave sensor that is attached to the seal gland through a stress-wave waveguide.

In applications where access to seal gland 24 is obstructed or dangerous, sensor 52 can be connected to seal gland 24 by means of stress-wave waveguide 92 shown in FIG. 12. Waveguide 92 is attached to seal gland 24 and its other end is attached to sensor mount 91. Sensor 52 is attached to sensor mount 91. Stress waves propagate well through long and thin waveguides that can be bent to a shape required to reach a location that is accessible. One skilled in the art would realize that waveguide 92 can be attached to seal parts other than gland 24 and can also be attached directly to wear probe 36.

I claim:

1. A method of monitoring a mechanical seal, which provides a seal between a rotating machine part and another machine part, to determine whether at least one seal face of said mechanical seal is worn, said method including the steps of:
   (a) providing at least one wear probe operably associated with at least one rotating component of said mechanical seal, said at least one wear probe being movable relative to said at least one rotating component, said at least one wear probe being configured to move relative to said at least one seal face independent of any wear of said at least one seal face, said at least one wear probe being configured to cause stress waves to be induced only when said at least one wear probe is in contact with said at least one rotating component;
   (b) providing at least one stress-wave sensor for measuring the intensity of stress waves induced by said at least one wear probe when it contacts said at least one rotating component;
   (c) moving said at least one wear probe relative to said at least one rotating component so that the distance between said at least one wear probe and said at least one rotating component decreases;
   (d) measuring a stress-wave signal with said at least one stress-wave sensor at any time during or subsequent to step (c); and,
   (e) evaluating the stress-wave signal measured in step (d) to determine if said mechanical seal is worn.

2. A method as recited in claim 1, further including the steps of:
   (a) specifying a wear level of at least one seal face of said mechanical seal that if reached or exceeded, the seal face is considered worn;
   (b) moving said at least one wear probe relative to said at least one rotating component a set distance such that said wear probe will contact said rotating component if the wear of said seal face reached or exceeded the wear level specified in step (a) of this claim.

3. A method as recited in claim 2, further including the steps of:
   (a) measuring at least one stress-wave signal before moving said at least one wear probe relative to said at least one rotating component;
   (b) measuring at least one stress-wave signal after said moving step (b) in claim 2; and, (c) evaluating stress-wave signals measured in step (a) of this claim and step (b) of this claim to determine if said at least one wear probe contacted said rotating component thus indicating that said seal face is worn.

4. A method as recited in claim 2, wherein:
(a) in step (b) of claim 2 said rotating component moves toward said wear probe and said wear probe remains stationary.

5. A method as recited in claim 2, further including the steps of:
(a) measuring the distance that said at least one wear probe has to move relative to said at least one rotating component to contact said at least one rotating component when said at least one seal face is unworn; and,
(b) moving said at least one wear probe relative to said at least one rotating component a set distance equal to the distance measured in step (a) of this claim less the wear level, measured as decrease of thickness of seal face material, that is specified in step (a) of claim 2.

6. A method as recited in claim 1, further including the step of:
(a) providing a force-limiting member to limit the maximum force that said wear probe can apply on said at least one rotating component of said mechanical seal.

7. A method as recited in claim 1, further including the step of:
(a) providing an instrumentation system operably associated with said at least one stress-wave sensor; and,
(b) automatically changing the gain of said instrumentation system so as to provide accurate measurement of the signal without a prior knowledge of the signal level that is to be measured.

8. A method as recited in claim 1, further including the steps of:
(a) providing an actuator and a monitoring computer, the actuator moves said at least one wear probe relative to said at least one rotating component in response to commands from the monitoring computer, the monitoring computer executes the acquisition and processing of the signal from the stress-wave sensor and evaluates the wear of said at least one seal face.

9. A method as recited in claim 8, wherein:
(a) said actuator limits the force that said at least one wear probe can apply on the at least one rotating component of the mechanical seal.

10. A method as recited in claim 1, further including the steps of:
(a) providing first and second wear probes;
(b) specifying a first wear level to be detected by said first wear probe;
(c) specifying a second wear level to be detected by said second wear probe, said second wear level being different from said first wear level.

11. A method as recited in claim 1, further including the steps of:
(a) providing at least two wear probes; and,
(b) using at least one of the at least two wear probes for removing deposits from the surface of said rotating component.

12. A method as recited in claim 1, wherein:
(a) said mechanical seal is a cartridge mechanical seal.

13. A method as recited in claim 1, wherein:
(a) said mechanical seal includes one of (i) at least one stationary seal face and at least one rotating seal seat, and (ii) at least one stationary seal seat and at least one rotating seal face.

14. A method as recited in claim 1, wherein:
(a) said at least one stress-wave sensor is connected to said at least one wear probe or to said mechanical seal through a stress-wave waveguide.

15. A method as recited in claim 1, further including the step of:
(a) providing said at least one rotating component with a textured surface that can be contacted by said at least one wear probe.

16. A method of monitoring a mechanical seal, which provides a seal between a rotating machine part and another machine part, to determine whether at least one seal face of said mechanical seal is worn, said method including the steps of:
(a) providing at least one wear probe operably associated with at least one rotating component of said mechanical seal, said at least one wear probe being movable relative to said at least one rotating component, said at least one wear probe being configured to move relative to said at least one seal face independent of any wear of said at least one seal face, said at least one wear probe being configured to cause stress waves to be induced only when said at least one wear probe is in contact with said at least one rotating component;
(b) providing at least one stress-wave sensor for measuring the intensity of stress waves induced by said at least one wear probe when it contacts said at least one rotating component;
(c) providing means for gradually moving said at least one wear probe toward said at least one rotating component;
(d) providing means for continuously measuring the distance that said at least one wear probe is moved;
(e) gradually moving said at least one wear probe toward said at least one rotating component while evaluating the stress-wave signal measured by said at least one stress-wave sensor;
(f) detecting the time when the intensity of stress-wave signal measured and evaluated in step (e) of this claim increases;
(g) determining the distance that said wear probe moved at the time detected in step (f) of this claim; and,
(h) evaluating the distance determined in step (g) of this claim to determine the wear level of said at least one seal face.

17. A method as recited in claim 16, further including the step of:
(a) providing a force-limiting member to limit the maximum force that said at least one wear probe can apply on said at least one rotating component of said mechanical seal.

18. A method as recited in claim 16, further including the steps of:
(a) providing an actuator and a monitoring computer, the actuator moves the at least one wear probe in response to commands from the monitoring computer that executes the acquisition and processing of the signal from the stress-wave sensor and evaluates the wear of said at least one seal face.

19. A method as recited in claim 16, further including the steps of:
(a) measuring the distance that said at least one wear probe has to move to contact the said at least one rotating component when said at least one seal face is unworn; and,
(b) determining the wear level, measured as decrease of thickness of seal face material, in step (h) of claim 16 by subtracting the distance determined in step (g) of claim 16 from the distance measured in step (a) of this claim.

20. A method as recited in claim 16, wherein:
(a) said at least one stress-wave sensor is connected to said wear probe or to said mechanical seal through a stress-wave waveguide.

21. A method as recited in claim 16, further including the step of:
(a) providing said at least one rotating component with a textured surface that can be contacted by said at least one wear probe.

22. An apparatus for monitoring a mechanical seal, which provides a seal between a rotating machine part and another machine part, to determine whether at least one seal face of said mechanical seal is worn, said apparatus comprising:
(a) at least one wear probe operably associated with at least one rotating component of said mechanical seal, said at least one wear probe being movable relative to said at least one rotating component, said at least one wear probe being configured to move relative to said at least one seal face independent of any wear of said at least one seal face, said at least one wear probe being configured to cause stress waves to be induced only when said at least one wear probe is in contact with said at least one rotating component;
(b) at least one sensor for measuring the intensity of a first signal induced by said at least one wear probe when contacting said at least one rotating component;
(c) an actuator for moving said at least one wear probe relative to said at least one rotating component so that said at least one wear probe and said at least one rotating component contact each other, said actuator and said wear probe being configured such that the force generated when said at least one wear probe contacts said at least one rotating component is substantially less than a force sufficient to damage said mechanical seal; and,
(d) means for measuring and evaluating said first signal to determine if said mechanical seal is worn.

* * * * *